United States Patent [19]

Garland et al.

[11] 4,348,388

[45] Sep. 7, 1982

[54] 11-AMINO-11-DEOXYDAUNORUBICIN AND ANALOGS

[75] Inventors: Robert B. Garland, Northbrook; Raphael Pappo, Skokie; Paul B. Sollman, Wilmette, all of Ill.

[73] Assignee: G.D. Searle & Co., Skokie, Ill.

[21] Appl. No.: 136,620

[22] Filed: Apr. 2, 1980

[51] Int. Cl.³ .................. A61K 31/70; C07H 15/24
[52] U.S. Cl. .................. 424/180; 260/365; 260/396 R; 260/429 R; 536/6.4
[58] Field of Search .................. 424/180; 536/17 A

[56] References Cited

U.S. PATENT DOCUMENTS

| | | | |
|---|---|---|---|
| 3,590,028 | 6/1971 | Arcamone et al. | 536/17 A |
| 4,031,211 | 6/1977 | Patelli et al. | 536/17 A |
| 4,046,878 | 9/1977 | Patelli et al. | 536/17 A |

FOREIGN PATENT DOCUMENTS

| | | | |
|---|---|---|---|
| 1003383 | 9/1965 | United Kingdom | 536/17 A |
| 1217133 | 12/1970 | United Kingdom | 536/17 A |

Primary Examiner—Johnnie R. Brown

Attorney, Agent, or Firm—Albert Tockman; W. Dennis Drehkoff; Albin James Nelson

[57] ABSTRACT

11-Amino-11-deoxydaunorubicin and analogs represented by the formula:

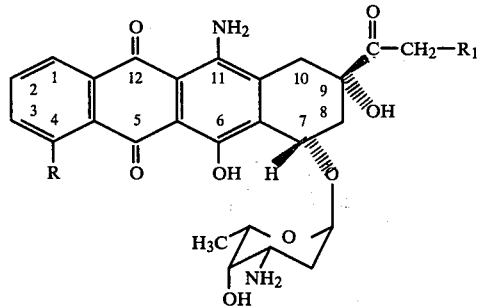

wherein: R is hydrogen, hydroxy or methoxy; $R_1$ is hydrogen or hydroxy; and the pharmaceutically acceptable salts thereof.

The compounds are useful in ameliorating tumor growth.

17 Claims, No Drawings

11-AMINO-11-DEOXYDAUNORUBICIN AND ANALOGS

BACKGROUND OF THE INVENTION

Adriamycin is one of the most widely used and useful anti-tumor drugs available. However, because of its cardiac toxicity, its use is limited. Various investigators have sought analogs of adriamycin which retain the antitumor activity of the parent antibiotic but which lack the undesirable cardiac toxicity. See for example, U.S. Pat. No. 4,046,878 which discloses daunorubicin derivatives, including 4-demethoxydaunorubicin and British Pat. No. 1,003,383 which discloses daunorubicin.

In addition to the search for agents with lessened toxicity, analogs which do not exhibit cross-resistivity to tumors which have become resistant to treatment with adriamycin, daunorubicin or 4-demethoxydaunorubicin continues.

The present invention provides analogs of daunorubicin and adriamycin.

SUMMARY OF THE DISCLOSURE

The present invention provides 11-amino-11-deoxydaunorubicin derivatives and intermediates useful in their preparation. The compounds are useful as agents which ameliorate tumor growth.

DETAILED DESCRIPTION OF PREFERRED EMBODIMENTS

The present invention provides 11-amino-11-deoxydaunorubicin analogs represented by Formula I:

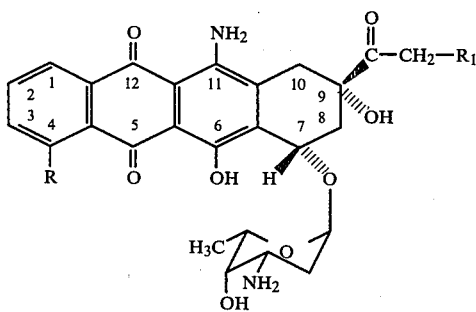

wherein: R is hydrogen, hydroxy or methoxy; $R_1$ is hydrogen or hydroxy; and the pharmaceutically acceptable salts thereof.

The term "pharmaceutically acceptable salts" refers to non-toxic acid addition salts of the compounds of this invention which are generally prepared by reacting the free base with a suitable organic or inorganic acid, or in situ during the final purification. Representative salts include the hydrochloride, hydrobromide, sulfate, bisulfate, laurate, borate, benzoate, lactate, phosphate, tosylate, citrate, maleate, fumarate, tartrate, napsylate and the like salts. It will be understood that the per-salts are included within the term, i.e. dihydrochloride, etc.

Compounds of Formula I are useful as agents to ameliorate tumor growth in mammals when administered parenterally, i.e. intravenously, at doses of from 40 to 50 mg/m² as a single intravenous injection administered at 21 day intervals or 20 mg/m² on each of three successive days repeated every four weeks.

Intermediates useful in the preparation of compounds of Formula I are represented by Formula II:

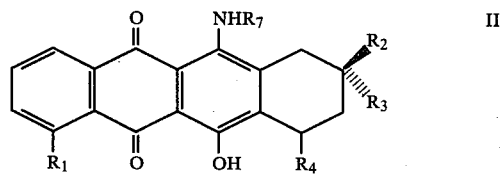

wherein $R_1$ is hydrogen, hydroxy or methoxy; $R_2$ is ethynyl or acetyl; $R_3$ is acetyl or hydroxy; and $R_4$ is hydroxy, trimethylsilyl or

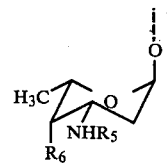

wherein: $R_5$ is hydrogen or trifluoroacetyl; $R_6$ is 4-nitrobenzoyloxy or hydroxy; and $R_7$ is hydrogen or trifluoroacetyl.

The preparation of the compounds of the present invention is summarized in the following reaction schemes:

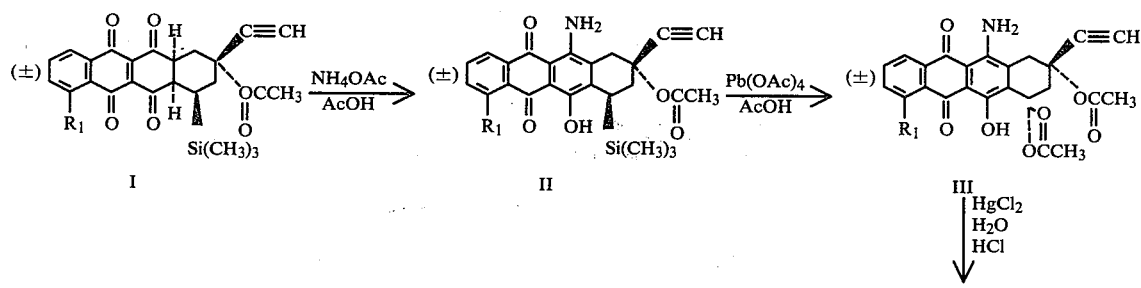

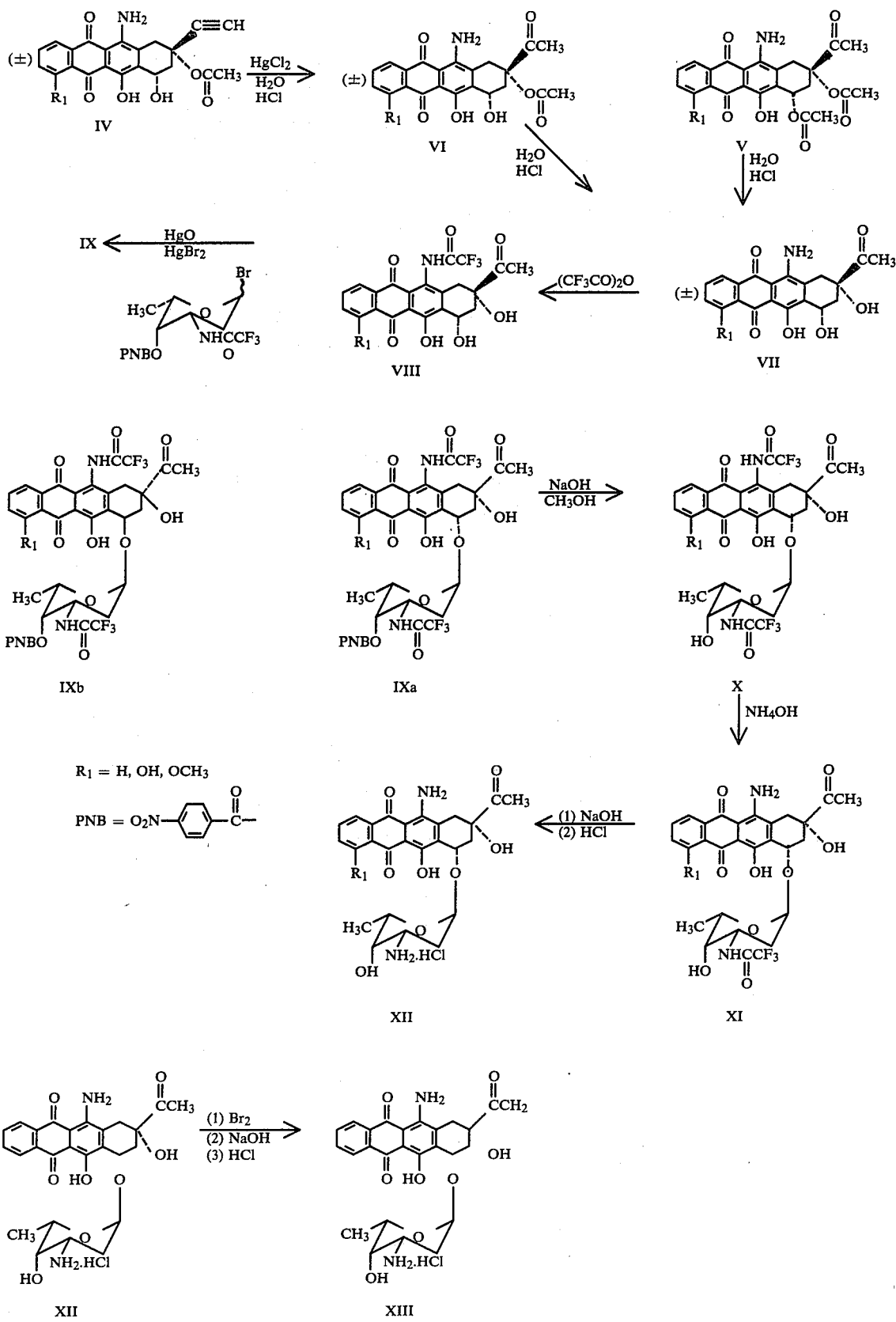

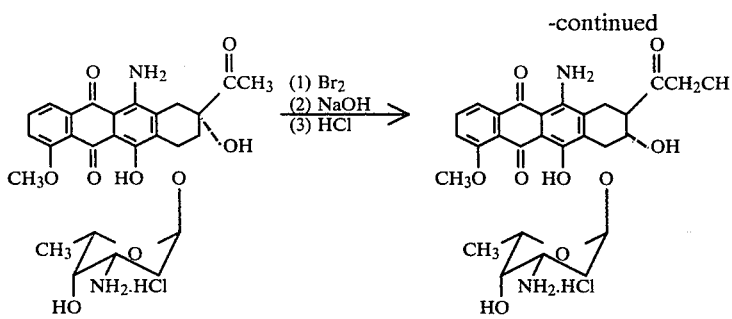

-continued

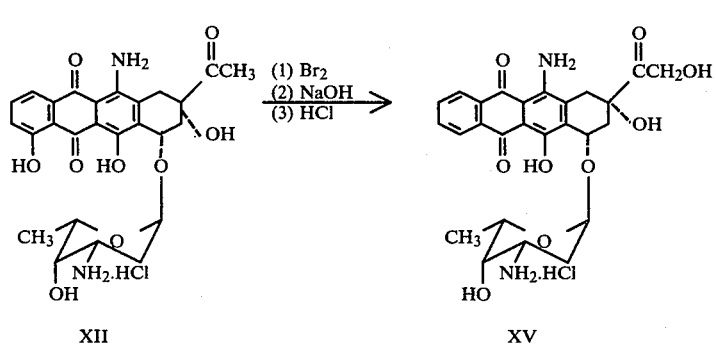

The following examples further illustrate the present invention. The Roman numerals used in the examples correspond to those used to identify compounds in the preceding reaction scheme.

EXAMPLE 1

Preparation of trans-(±)-9-(acetyloxy)-11-amino 9-ethynyl-7,8,9,10-tetrahydro-6-hydroxy-7-(trimethylsilyl)-5,12-naphthacenedione (II)

To a solution of 1717 parts by weight of (±)-3-β-(acetyloxy)-3-ethynyl-1,2,3,4,4aβ,12aβ-hexahydro-1α-(trimethylsilyl)-5,6,11,12-naphthacenetetrone(I) in 60,000 parts by volume of acetic acid at 90° C. is added 15,000 parts by weight of ammonium acetate with vigorous stirring. After 5 minutes, the mixture is cooled to 20° C. and diluted with 130,000 parts by volume of water. After 30 minutes of stirring, the solid is collected by filtration, washed thoroughly with water and dried. The crude material is purified by column chromatography on 18,000 parts by weight of neutral silicic acid, 100–200 mesh, developed with a gradient of 1% to 10% (v/v) of ethyl acetate in methylene chloride. The fractions containing the major product are crystallized from methylene chloride-ethyl ether to give trans-(±)-9-(acetyloxy)-11-amino-9-ethynyl-7,8,9,10-tetrahydro-6-hydroxy-7-(trimethylsilyl)-5,12-naphthacenedione (II), m.p. 241°–243° C.(decomp.).

EXAMPLE 2

Preparation of cis-(±)-7,9-bis(acetyloxy)-11-amino-9-ethynyl-7,8,9,10-tetrahydro-6-hydroxy-5,11-naphthacenedione(III)

A solution of 0.65 parts by weight of approximately 95% lead tetraacetate and 0.3 parts by weight of potassium acetate in 30 parts by volume of acetic acid and 1 part by volume of acetic anhydride is stirred at ambient temperature overnight. After being cooled to 15° C., 0.57 parts by weight of trans-(±)-9-(acetyloxy)-11-amino-9-ethynyl-7,8,9,10-tetrahydro-6-hydroxy-7-(trimethylsilyl)-5,12-naphthacenedione (II) is added with stirring and the cooling bath is removed. After 2 hours, 0.05 parts by weight of sodium bisulfate is added and the mixture is stirred for an additional hour and is then diluted with 10 parts by volume of water. After stirring for an additional hour, the solid is collected by filtration, washed well with water and dried. This crude material is crystallized from methylene chloride-ethyl ether to yield pure cis-(±)-7,9-bis(acetyloxy)-11-amino-9-ethynyl-7,8,9,10-tetrahydro-6-hydroxy-5,12-napthacenedione (III), m.p. 251°–254° C.(decomp).

EXAMPLE 3

Preparation of cis-(±)-9-(acetyloxy)-11-amino-9-ethynyl-7,8,9,10-tetrahydro-6,7-dihydroxy-5,12-naphthacenedione(IV)

A methylene chloride extract of the mother liquors of Example 2 is combined with the crystallization filtrate and evaporated. The residue is chromatographed on a column of 10 parts by weight of neutral silicic acid, 100–200 mesh, developing with 5%(v/v) ethyl acetate in methylene chloride. The first fraction eluted is crystallized from methylene chloride-ethyl ether to yield additional product of Example 2. The second fraction eluted is crystallized from methylene chloride-ethyl ether to yield cis-(±)-9-(acetyloxy)-11-amino-9-ethynyl-7,8,9,10-tetrahydro-6,7-dihydroxy-5,12-naphthacenedione(IV), m.p. 228°–230° C.(decomp.)

EXAMPLE 4

Preparation of cis-(±)-9-acetyl-7,9-bis(acetyloxy)-11-amino-7,8,9,10-tetrahydro-6-hydroxy-5,12-naphthacenedione(V)

A mixture of 1.4 parts by weight of mercuric chloride, 1.08 parts by weight of cis-(±)-7,9-bis(acetyloxy)-11-amino-9-ethynyl-7,8,9,10-tetrahydro-6-hydroxy-5,12-naphthacenedione(III), 10 parts by volume of water and 200 parts by volume of methylene chloride is stirred vigorously for 18 hours at ambient temperatures. After the addition of 50 parts of 10%(w/v) hydrochloric acid and thorough mixing, the organic layer is separated, washed with water and dried over sodium sulfate. After evaporation to dryness, the product is crystallized from methylene chloride-ethyl ether to yield cis-(±)-9-acetyl-7,9-bis-(acetyloxy)-11-amino-7,8,9,10-tetrahydro-6-hydroxy-5,12-naphthacenedione(V), m.p. 258°-260° C.(decomp.).

EXAMPLE 5

Preparation of cis-9-acetyl-11-amino-7,8,9,10-tetrahydro-6,7,9,-trihydroxy-5,12-naphthacenedione (VII)

A suspension of 1.15 parts by weight of cis-(±)-9-acetyl-7,9-bis(acetyloxy)-11-amino-7,8,9,10-tetrahydro-6-hydroxy-5,12-naphthacenedione(V) in 200 parts by volume of tetrahydrofuran, 20 parts by volume of water, and 10 parts by volume of concentrated hydrochloric acid is refluxed for 2 days. After cooling and dilution with 100 parts by volume of water, the mixture is extracted twice with 200 parts by volume of methylene chloride. After washing with water and drying over sodium sulfate, the extracts are concentrated to a small residue which is triturated with a mixture of 50 parts by volume of ethyl ether and 50 parts by volume of hexane to yield the cis-9-acetyl-11-amino-7,8,9,10-tetrahydro-6,7,9-trihydroxy-5,12-naphthacenedione (VII).

EXAMPLE 6

Preparation of cis-(±)-9-acetyl-9-(acetyloxy)-11-amino-7,8,9,10-tetrahydro-6,7-dihydroxy-5,12-naphthacenedione (VI)

A mixture of 0.9 parts by weight of cis-(±)-9-(acetyloxy)-11-amino-9-ethynyl-7,8,9,10-tetrahydro-6,7-dihydro-5,12-naphthacenedione(IV), 1.5 parts by weight of mercuric chloride, 10 parts by volume of water and 250 parts by volume of methylene chloride is stirred vigorously for 18 hours at ambient temperatures. After the addition of 50 parts by volume of 10%(w/v) hydrochloric acid and thorough mixing, the organic layer is separated, washed well with water and dried over sodium sulfate. The resulting solution is concentrated to about 10 parts by volume and then is diluted with 50 parts by volume of ether. The solid is collected by filtration, washed with ether and dried to yield cis-(±)-9-(acetyloxy)-11-amino-7,8,9,10-tetrahydro-6,7-dihydroxy-,12-naphthacenedione(VI) which sinters at 260° C.

EXAMPLE 7

Preparation of cis-(±)-9-acetyl-11-amino-7,8,9,10-tetrahydro-6,7,9-trihydroxy-5,12-naphthacenedione (VII)

A suspension of 0.8 parts by weight of cis-(±)-9-acetyl-9-(acetyloxy)-11-amino-7,8,9,10-tetrahydro-6,7-dihydroxy-5,12-naphthacenedione(VI) in 200 parts by volume of tetrahydrofuran, 20 parts by volume of water and 10 parts by volume of concentrated hydrochloric acid is refluxed for 6 hours. After cooling and dilution with 100 parts by volume of water, the mixture is extracted twice with 200 parts by volume of methylene chloride. After washing with water and drying over sodium sulfate, the extracts are concentrated to a small residue which is triturated with a mixture of 50 parts by volume of ethyl ether and 50 parts by volume of hexane to yield cis-(±)-9-acetyl-11-amino-7,8,9,10-tetrahydro-6,7,9-trihydroxy-5,12-naphthacenedione(VII).

EXAMPLE 8

Preparation of cis-(±)-9-acetyl-11-[(trifluoroacetyl)amino]-7,8,9,10-tetrahydro-6,7,9-trihydroxy-5,12-naphthacenedione(VIII)

To a stirred suspension of 1.77 parts by weight of cis(±)-9-acetyl-11-amino-7,8,9,10-tetrahydro-6,7,9-trihydroxy-5,12-naphthacenedione(VIII) in 300 parts by volume of methylene chloride, chilled at 0 C., is added 2 parts of trifluoroacetic anhydride. When solution is complete (usually 5–10 minutes), the mixture is removed from the cooling bath and evaporated under a vigorous nitrogen stream without heating. The residue is chromatographed on 500 parts by weight of neutral silicic acid (100–200 mesh). After eluting traces of biproducts with 15%(v/v) ethyl acetate in toluene, the product is eluted with 20%(v/v) ethyl acetate in toluene. Crystallization from methylene chloride yields the cis-(±)-9-acetyl-11-[(trifluoroacetyl)amino]-7,8,9,10-tetrahydro-6,7,9-trihydroxy-5,12-naphthacenedione(VIII).

EXAMPLE 9

Preparation of cis-9-acetyl-11[(trifluoroacetyl)amino]-7S-{2,3,6-trideoxy-3-[(trifluoroacetyl)amino]-4-0-(4-nitrobenzoyl)-α-L-lyxo(hexopyranosyl)oxy}-7,8,9,10-tetrahydro-6,9-dihydroxy-5,12-naphthacenedione(IXa) and the corresponding 7R,9R isomer (IXb)

To a suspension of 5 parts by weight of mercuric oxide, 2 parts by weight of mercuric bromide, 40 parts by weight of 3A molecular sieves(freshly dried at 150° C. for 4 hours) and 11 parts by weight of cis-(±)-9-acetyl-11-[(trifluoroacetyl)amino]-7,8,9,10-tetrahydro-6,7,9-trihydroxy-5,12-naphthacenedione(VIII) in 400 parts by volume of methylene chloride is added a solution of approximately 17 parts by weight of freshly prepared 2,3,6-trideoxy-3-[(trifluoroacetyl)amino]-4-O-(4-nitrobenzoyl)-L-lyxo-hexopyranosyl bromide prepared by the method of Acton et al., *J. Med. Chem.*, 17, 659(1974), in 500 parts by volume of methylene chloride. The mixture is stirred vigorously for 30 minutes and the solids are removed by filtration. The filtrate is washed with water and then dried over sodium sulfate and subsequently evaporated to dryness. The residue is chromatographed on 900 parts by weight of neutral silicic acid(100–200 mesh) developing with 10%(v/v) ethyl acetate in toluene to separate the two major products. The first fraction eluted is cis-9-acetyl-11-[(trifluoroacetyl)amino]-7S-{2,3,6-trideoxy-3-[(trifluoroacetyl)amino]-4-O-(4-nitrobenzoyl)-α-L-lyxo-hexopyranosyloxy}-7,8,9,10-tetrahydro-6,9-dihydroxy-5,12-naphthacenenedione(IXa)contaminated only by trace biproducts.

The second fraction eluted is the isomeric product, cis-9-acetyl-11-[(trifluoroacetyl)amino]-7R-{2,3,6-trideoxy-3-[(trifluoroacetyl)amino]-4-O-(4-nitrobenzoyl)-α-L-lyxo-hexopyranosyl]oxy}-7,8,9,10-tetrahydro-6,9-dihydroxy-5,12-naphthacenedione(IXb).

EXAMPLE 10

Preparation of
cis-7S-{2,3,6-trideoxy-3-[(trifluoroacetyl)amino]-α-L-lyxo-hexopyranosyl]oxy}-11-[(trifluoroacetyl)amino]-7,8,9,10-tetrahydro-6,9-dihydroxy-5,12-naphthacenedione (X)

A solution of 8.6 parts by weight of Compound IXa in 500 parts by volume of methanol is chilled in an ice bath at 0° C. while 200 parts by volume of 0.1 N sodium hydroxide is added with stirring. After 10 minutes, 200 parts by volume of 0.1 N hydrochloric acid is added and the mixture is extracted twice with methylene chloride and the extracts washed with water, dried over sodium sulfate and evaporated. The resulting residue is chromatographed on 900 parts by weight of neutral silicic acid (100–200 mesh) developing with 30%(v/v) of ethyl acetate in methylene chloride. Traces of by-products are readily separated and the major fraction is crystallized from methylene chloride to yield cis-7S-{[2,3,6-trideoxy-3-[(trifluoro-acetyl)amino]-α-L-lyxo-hexopyranosyl]oxy}-11-[(trifluoroacetyl)-amino]-7,8,9,10-tetrahydro-6,9-dihydroxy-5,12-naphthacenedione(X), m.p. 171–173 C.; $[\alpha]_D^{25}+93.3$ (c, 0.1%, dioxane); NMR(CDCl$_3$) δ1.49d (3H, J=6 Hz), 2.32s(3H), 2.91d (1H, J=18.5 Hz). 3.20d(1H, J=18.5 Hz), 5.34 broad t(1H, J=2.0 Hz), 5.56 broad t(1H, J=2.2 Hz); U.V. vis. in methanol, maxima at 227, 256, 404 nm, shoulder at 282.5 nm ($\epsilon$=21,790, 30,580, 5,680 and 10,520, respectively.

EXAMPLE 11

Preparation of
cis-9-acetyl-11-amino-7S-{[2,3,6-trideoxy-3-[(trifluoroacetyl)amino]-α-L-lyxo-hexopyranosyl]oxy}-7,8,9,10-tetrahydro-6,9-dihydroxy-5,12-naphthacenedione (XI)

A solution of 4.3 parts by weight of the product of Example 10(X) in 300 parts by volume of methanol is stirred with 15 parts by volume of concentrated ammonium hydroxide for 5 hours at ambient temperature. After dilution with 300 parts of water, the mixture is extracted several times with methylene chloride. The extracts are washed well with water, dried over sodium sulfate, and evaporated leaving a residue of cis-9-acetyl-11-amino-7S-{[2,3,6-trideoxy-3-[(trifluoroacetyl)amino]-αL-lyxo-hexopyranosyl]oxy}-7,8,9,10-tetrahydro-6,9-dihydroxy-5,12-naphthacendione (XI).

EXAMPLE 12

Preparation of
cis-9-acetyl-11-amino-7S-{[2,3,6-trideoxy-3-α-L-lyxo-hexopyranosyl]oxy}-7,8,9,10-tetrahydro-6,9-dihydroxy-5,12-naphthacenedione hydrochloride (XII)

The latter product(XI) is taken up in 50 parts by volume of methanol and treated with 250 parts by volume of 0.1 N sodium hydroxide for one hour at ambient temperatures. The mixture is neutralized to pH 8 by the addition of 0.1 N hydrochloric acid and then extracted 3 times with 500 parts by volume of methylene chloride. After washing with a small amount of water and drying over sodium sulfate, the solution is concentrated to approximately 200 parts by volume. A solution of 1 part by volume of 6 N hydrogen chloride in isopropanol in 200 parts of ethyl ether is added with vigorous stirring. The resultant solid is collected by filtration and washed with ethyl ether to yield cis-9-acetyl-11-amino-7S-{[2,3,6,-trideoxy-3-[(trifluoroacetyl)amino]-α-L-lyxo-hexopyranosyl]oxy}-7,8,9,10-tetrahydro-6,9-dihydroxy-5,12-naphthacenedione hydrochloride (XII), as the monohydrate, m.p. 189–192 C.: $[\alpha]_D^{25}+514°$ (c, 0.04%, methanol); IR(KBr) 1589,1610,1718 cm$^{-1}$; UV-visible in methanol, maxima at 253.5, 280, 532, 565 nm and shoulders at 231 and 500 nm ($\epsilon$=41,200, 10,020,12,180, 10,630, 22,840 and 8,500 respectively.

EXAMPLE 13

Preparation of
cis-9-acetyl-11-amino-7S-[(3-amino-2,3,6-trideoxy-α-L-lyxo-hexopyranosyl)oxy]-7,8,9,10-tetrahydro-6,9-dihydroxy-4-methoxy-5,12-naphthacenedione hydrochloride (XII, R=OCH$_3$, R$_1$=H)

Substituting (±)-9β-(acetyloxy)-9-ethynyl-6aβ,7,8,9,10,10aβ-hexahydro-4-methoxy-7α-(trimethylsilyl)-5,6,11,12-naphthacenetetrone (I,R=OCH$_3$) for the starting intermediate of Example 1 and substantially repeating the procedures followed in Examples 1–12 yields the desired product as the hydrochloride salt.

EXAMPLE 14

Preparation of
cis-9-acetyl-11-amino-7S-[(3-amino-2,3,6-trideoxy-α-L-lyxo-hexopyranosyl)oxy]-7,8,9,10-tetrahydro-4,6,9-trihydroxy-5,12-naphthacenedione hydrochloride (XII, R=OH, R$_1$=H)

Substituting (±)-9β-(acetyloxy)-9-ethynyl-6aβ,7,8,9,10,10aβ-hexahydro-4-hydroxy-7α-(trimethylsilyl)-5,6,11,12-naphthacenedtetrone(I, R=OH) for the starting intermediate of Example 1(I, R-H) and substantially repeating the procedures of Examples 1–12, the desired product is obtained.

EXAMPLE 15

Preparation of
cis-11-amino-7S-[(3-amino-2,3,6-trideoxy-α-L-lyxo-hexopyranosyl)oxy]-7,8,9,10-tetrahydro-6,9-dihydroxy-9(hydroxyacetyl)-5,12-naphthacenediene hydrochloride (XIII)

A solution of 11 parts by weight of cis-9-acetyl-11-amino-7S-[(3-amino-2,3,6-trideoxy-α-L-lyxo-hexopyranosyl)oxy]-7,8,9,10-tetrahydro-6,9-dihydroxy-5,12-naphthacenedione chloride (XII,R$_1$=H,R$_1$=H) in 300 parts by volume of methanol and 1000 parts by volume of dioxane is treated with a solution of 3.1 parts by weight of bromine in 40 parts by volume of methylene chloride for 4 hours at ambient temperatures. The mixture is concentrated to dryness under reduced pressure and the residue is triturated with 50 parts by volume of methylene chloride and then diluted with 200 parts by volume of ethyl ether. The crude product is collected by filtration, washing well with ethyl ether. To a solution of this material in 1500 parts by volume of methanol and 700 parts by volume of water is added sufficient 0.1 N sodium hydroxide solution to raise the pH to 10–10.5 and maintain it there for 20 minutes while under an inert atmosphere. At this point the mixture is diluted with 1000 parts more water and extracted repeatedly with methylene chloride until little more color is in the extract. After washing with a small amount of water the extracts are dried over sodium sulfate and concentrated under reduced pressure to approximately 50 parts by volume. A solution of 0.4 parts by volume of 6 N hydrogen chloride in isopropanol in 50 parts by volume of ethyl ether is added with vigorous stirring. The resultant solid is collected by filtration and washed with ethyl ether to yield cis-11-amino-7S-[(3-amino-2,3,6-trideoxy-α-L-lyxo-hexopyranosyl)oxy]-7,8,9,10-tetrahydro-6,9-dihydroxy-9-(hydroxyacetyl)-5,12-naphthacenedione hydrochloride (XIII) as a hydrate.

EXAMPLE 16

Preparation of cis-amino-7S-[(3-amino-2,3,6-trideoxy-α-L-lyxo-hexopyranosyl)oxy]-7,8,9,10-tetrahydro-6,9-dihydroxy-9-(hydroxyacetyl)-4-methoxy-5,12-naphthacenedione hydrochloride(XIV)

Substituting cis-9-acetyl-11-amino-7S-[(3-amino-2,3,6-trideoxy-α-L-lyxo-hexopyranosyl)oxy]-7,8,9,10-tetrahydro-6,9-dihydroxy-4-methoxy-5,12-naphthacenedione hydrochloride (XII,R=CH$_3$O, R$_1$=H) for the starting material (XII,R=OH) of Example 15 gives cis-11-amino-7S-[(3-amino-2,3,6-trideoxy-α-L-lyxo-hexopyranosyl)oxy]7,8,9,10-tetrahydro-6,9-dihydroxy-9-(hydroxyacetyl)-4-methoxy-5,12-naphthacenedione hydrochloride (XIV,R=CH$_3$O,R$_1$=OH).

The R values for the compounds of Examples 1–15 are summarized in Tables I and II as follows:

TABLE 1

R Values for Intermediates of Formula II

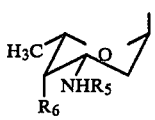

| Compound | Example Number | $R_1$ | $R_2$ | $R_3$ | $R_4$ | $R_5$ | $R_6$ | $R_7$ |
|---|---|---|---|---|---|---|---|---|
| I | 1 | H | —C≡CH | —OCCH$_3$ (O) | Si(CH$_3$)$_3$ | — | — | — |
| II | 1 | H | —C≡CH | —OCCH$_3$ (O) | Si(CH$_3$)$_3$ | — | — | H |
| III | 2 | H | —C≡CH | —OCCH$_3$ (O) | OCCH$_3$ (O) | — | — | H |
| IV | 3 | H | —C≡CH | —OCCH$_3$ (O) | —OH | — | — | H |
| V | 4 | H | —CCH$_3$ (O) | —OCCH$_3$ (O) | OCCH$_3$ (O) | — | — | H |
| VI | 6 | H | —CCH$_3$ (O) | —OCCH$_3$ (O) | —OH | — | — | H |
| VII | 5,7 | H | —CCH$_3$ (O) | —OH | —OH | — | — | H |
| VIII | 8 | H | —CCH$_3$ (O) | —OH | —OH | — | — | CCF$_3$ (O) |
| IXa | 9 | —H | —CCH$_3$ (O) | —OH | (sugar) | CCF$_3$ (O) | O$_2$N—C$_6$H$_4$—CO— | CCF$_3$ (O) |
| IXb | 9 | H | —CCH$_3$ (O) | —OH | " | CCF$_3$ (O) | O$_2$N—C$_6$H$_4$—CO— | CCF$_3$ (O) |
| X | 10 | H | —CCH$_3$ (O) | —OH | " | CCF$_3$ (O) | OH | CCF$_3$ (O) |
| XI | 11 | H | —CCH$_3$ (O) | —OH | " | CCF$_3$ (O) | OH | H |

TABLE 2

R Values for 11-Amino-11-Deoxydaunorubicin Analogs of Formula I

| Compound | Example | R | $R_1$ |
|---|---|---|---|
| XII | 12 | H | H |
| XII | 13 | OCH$_3$ | H |
| XII | 14 | OH | H |
| XII | 15 | H | OH |
| XIV | 16 | OCH$_3$ | OH |
| XV | 17 | OH | OH |

EXAMPLE 17

Preparation of cis-11-amino-7S-[(3-amino-2,3,6-trideoxy-α-L-lyxo-hexopyranosyl)oxy]-7,8,9,10-tetrahydro-4,6,9-trihydroxy-9-(hydroxyacetyl)-5,12-naphthacenedione hydrochloride(XIV)

Substituting cis-9-acetyl-11-amino-7S-[(3-amino-2,3,6-trideoxy-α-L-lyxo-hexopyranosyl)oxy]-7,8,9,10-tetrahydro-4,6,9-trihydroxy-5,12-naphthacenedione hydrochloride (XII,R=OH,$R_1$=1) for the starting material of Example 15 and substantially repeating the procedures of example 15 gives cis-11-amino-7S-[(3-amino-2,3,6-trideoxy-α-L-lyxo-hexo-pyranosyl)oxy]-7,8,9,10-tetrahydro-4,6,9-trihydroxy-9-(hydroxyacetyl)-5,12-naphthacenedione hydrochloride (XIV,R=$R_1$=OH).

The starting intermediates, I, are known and can be prepared by the methods described in U.S. Pat. No. 4,161,480.

Tables 1 and 2 summarize the R values for compounds of Formulae I and II.

The antineoplastic activity of the compounds of this invention was first established against L-1210 leukemia. The relative activities against the L-1210 leukemia and the L cell cytotoxicity was determined and compared to that of adriamycin.

EXAMPLE 18

Comparison of Compound XII(R=H) Adriamycin and 4-Demethoxydaunorubicin Against L-1210 Leukemia Donor mice were implanted with L-1210 leukemia cells i.p. On the sixth day following implant, the mice were sacrificed. Tumor cells were collected from the peritoneal cavity, suspended in saline solution, and $10^5$ cells per mouse were implanted i.v. into $BDF_1$ male mice weighing 18–20 grams. Ten mice per treatment group were employed and the day of implantation considered as day 0. A single dose of test compound was administered by i.v. injection 24 hours following the implant of L-1210 tumor cells. The animals were observed and the survival pattern was compared with that of control mice which received the same tumor implant but were not treated with drug. Results are presented as %ILS (increase in life span over control animals) in Table 3 below.

TABLE 3

| Compound | Optimum Dose (μmoles/kg) | % ILS | Survivors at day 60 |
| --- | --- | --- | --- |
| Saline | 0 | 0 | 0 |
| Adriamycin | 33.6 | 100 | 0 |
| Ex. XII | 27 | 96 | 0 |
| 4-Demethoxy-daunorubicin | 4.5 | 83 | 0 |

The preferred route of administration is the intravenous route for Compound XII. The compound appears to be inactive against P-388 L-1210 leukemias when administered orally, and is less active when administered intraperitoneally.

EXAMPLES 19 AND 20

Comparison of the L-Cell Cytotoxicities of Compound XII(R=H) and Adriamycin

Expotentially growing L-cells were treated with dilutions of Compound XII and adriamycin and $ID_{50}$ (concentration of compounds giving 50% inhibition of cell growth) measured after 48 hours with the following results.

| | $ID_{50}$ (μg/ml) | |
| --- | --- | --- |
| Compound | Ex. 19 | Ex. 20 |
| Adriamycin | 0.063 | 0.100 |
| Ex. XII | 0.010 | 0.015 |

Pharmaceutical compositions for parenteral administration are provided via sterile fluid admixture of a tumor-growth ameliorating agent of the present invention with a suitable diluent, i.e. water, corn oil, propylene glycol, peanut oil, benzyl alcohol, saline, etc. and can include buffers and other adjuvants commonly employed in the art, or as lyophylized powders as illustrated by the following example.

EXAMPLE 21

Sterile vials ae prepared by standard methods containing:

| Ingredient | Mg |
| --- | --- |
| Ex. XII compound | 50 |
| Lactose | 250 | as a sterile, lyophilized powder.

I claim:

1. An 11-amino-11-deoxydaunorubicin derivative represented by the formula:

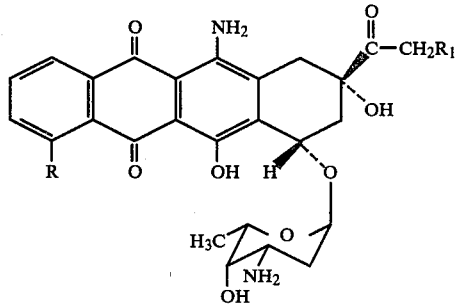

wherein: R is hydrogen, hydroxy or methoxy; $R_1$ is hydrogen or hydroxy; and the pharmaceutically acceptable salts thereof.

2. A compound of claim 1 wherein $R_1$ is hydrogen.
3. A compound of claim 1 wherein $R_1$ is hydroxy.
4. A compound of claim 1 wherein R is hydrogen.
5. A compound of claim 1 wherein R is hydroxy.
6. A compound of claim 1 wherein R is methoxy.
7. A compound of claim 1: cis-9-acetyl-11-amino-7S-[(3-amino-2,3,6-trideoxy-α-L-lyxo-hexopyranosyl)oxy]-7,8,9,10-tetrahydro-6,9-dihydroxy-5,12-naphthacenedione or a pharmaceutically acceptable salt thereof.
8. A compound of claim 1: cis-9-acetyl-11-amino-7S-[(3-amino-2,3,6-trideoxy-α-L-lyxo-hexopyranosyl)oxy]-7,8,9,10-tetrahydro-6,9-dihydroxy-4-methoxy-5,12-napthacenedione or a pharmaceutically acceptable salt thereof.
9. A compound of claim 1: cis-9-acetyl-11-amino-7S-[(3-amino-2,3,6-trideoxy-α-L-lyxo-hexopyranosyl)oxy]-7,8,9,10-tetrahydro-4,6,9-trihydroxy-5,12-naphthacenedione or a pharmaceutically acceptable salt thereof.

10. A compound of claim 1: cis-11-amino-7S-[(3-amino-2,3,6,-trideoxy-α-L-lyxo-hexopyranosyl)oxy]-7,8,9,10-tetrahydro-6,9,11-trihydroxy-9-(hydroxyacetyl)-5,12-naphthacenedione or a pharmaceutically acceptable salt thereof.

11. A compound of claim 1: cis-11-amino-7S-[(3-amino-2,3,6-trideoxy-α-L-lyxo-hexopyranosyl)oxy]-7,8,9,10-tetrahydroxy-9-(hydroxyacetyl)-5,12-naphthacenedione or a pharmaceutically acceptable salt thereof.

12. A compound of claim 1: cis-11-amino-7S-[(3-amino-2,3,6-trideoxy-α-L-lyxo-hexopyranosyl)oxy]-7,8,9,10-tetrahydro-6,9,11-tetrahydroxy-9-(hydroxyacetyl)-4-methoxy-5,12-naphthacenedione or a pharmaceutically acceptable salt thereof.

13. A pharmaceutical composition for parenteral administration comprising a therapeutically effective amount of a compound of claim 1 and a pharmaceutically acceptable carrier or diluent.

14. An 11-amino-11-deoxydaunorubicin intermediate represented by the formula

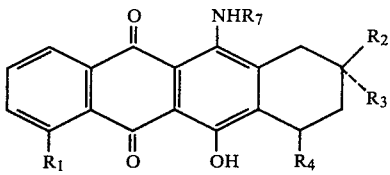

wherein: $R_1$ is hydrogen, hydroxy or methoxy; $R_2$ is ethynyl or acetyl; $R_3$ is acetyl or hydroxy; $R_4$ is

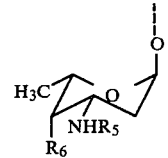

wherein $R_5$ is hydrogen or trifluoroacetyl and $R_6$ is 4-nitrobenzoyloxy or hydroxy; and $R_7$ is hydrogen or trifluoroacetyl, or a salt thereof when $R_5$ is hydrogen.

15. A compound of claim 14 wherein $R_1$ is hydrogen.
16. A compound of claim 14 wherein $R_1$ is hydroxy.
17. A compound of claim 14 wherein $R_1$ is methoxy.

* * * * *